United States Patent [19]
Beliard et al.

[11] Patent Number: 5,851,524
[45] Date of Patent: Dec. 22, 1998

[54] HUMAN MONOCLONAL ANTI-RHESUS (D) ANTIBODIES AND CELL LINES PRODUCING SAME

[75] Inventors: Roland Beliard, Saintes, France; Ulf Bethke, Rodermark, Germany; Dominique Bourel, La Madeleine, France; Ahmed Bouzidi, Annoeullin, France; Hervé Broly, Perenchies, France; Peter Byrne, Alsbach, Germany; Magali Holuigue, Samer, France; Michael Kloft; Detlef Rohm, both of Darmstadt, Germany

[73] Assignees: Association pour l'Essor de la Transfusion Sanguine dans la Region du Nord, Lille, France; BIOTEST Pharma GmbH, Dreieich, Germany

[21] Appl. No.: 798,444

[22] Filed: Feb. 10, 1997

Related U.S. Application Data

[63] Continuation of Ser. No. 196,061, Apr. 5, 1994, abandoned.

[30] Foreign Application Priority Data

Jun. 26, 1992 [FR] France .................................. 92 07893
Jul. 23, 1992 [DE] Germany ......................... 42 24 357.2

[51] Int. Cl.[6] .......................... A61K 39/395; C12N 5/00; C07K 16/00; C12P 21/08
[52] U.S. Cl. .................................. 424/142.1; 424/153.1; 424/173.1; 435/337; 435/343; 435/346; 530/388.15; 530/388.7
[58] Field of Search ..................... 435/337, 343, 435/346; 530/388.15, 388.7; 424/142.1, 173.1, 153.1

[56] References Cited

U.S. PATENT DOCUMENTS 4,634,664  1/1987  Oestberg .
5,487,891  1/1996  Bradley et al. .

FOREIGN PATENT DOCUMENTS 8902443   3/1989   WIPO .
8902600   3/1989   WIPO .
9011090  10/1990   WIPO .

OTHER PUBLICATIONS

McCann et al., J. Immunological Methods, 115 pp. 3–15 (1988).
Hadley et al., Immunology, 67, pp. 550–552 (1989).
Hughes–Jones, Blood Reviews, 3, pp. 53–58 (1989).
Kozbor et al. Immunol. Today vol. 4: 72–79, 1983.

*Primary Examiner*—Anthony C. Caputa
*Assistant Examiner*—Mark Navarro
*Attorney, Agent, or Firm*—Birch, Stewart, Kolasch & Birch, LLP

[57] ABSTRACT

The invention relates to 2 human monoclonal antibodies of sub-classes IgG1 and IgG3, against the Rhesus D antigen and to a pharmaceutical composition containing a mixture of the said antibodies, more particularly intended for the prophylaxis of the haemolytic disease of the newborn. The invention also relates to the heterohybridoma cell lines that produce these antibodies, which are filed with the "Deutsche Sammlung von Mikroorganismen und Zellkulturen" under accession numbers DSM AC 2039 and DSM AC 2040.

5 Claims, No Drawings

HUMAN MONOCLONAL ANTI-RHESUS (D) ANTIBODIES AND CELL LINES PRODUCING SAME

This application is a continuation of application Ser. No. 08/196,061 filed on Apr. 5, 1994, now abandoned.

The invention relates to human monoclonal antibodies against the Rhesus D antigen (Rh D) which is expressed on the surface of human red blood cells, and to a pharmaceutical composition containing same, intended for the prevention of the haemolytic disease of the newborn.

These antibodies are produced by heterohybrid cell lines obtained by the fusion of human B lymphocytes originating from Rhesus negative volunteers immunized with Rhesus positive red cells, with either murine myeloma or human/mouse heterohybrid myeloma cells.

The antibodies according to the invention can be used, prophylactically, for the protection of Rhesus negative women, before or immediately after the birth of a Rhesus positive child, to prevent haemolytic disease of the newborn (HDN) at the time of subsequent pregnancies. The antibodies according to the invention can also be used in diagnostic tests.

The invention thus generally relates to anti-D monoclonal antibodies, to the hybrid cells producing the said antibodies, to the methods of preparing the heterohybrids producing the said antibodies, and to pharmaceutical compositions or diagnostic tests including the said antibodies.

The antigens of blood groups are classified using several systems according to the nature of the membrane molecules expressed on the surface of the red blood cells. The Rhesus (Rh) system includes 5 molecules or antigens: D, C, c, E and e (ISSITT, 1988). The D antigen is the most important of these molecules because it is the most immunogenic, that is to say it can induce the production of anti-D antibodies if the Rh D positive red blood cells are transfused into Rh negative subjects.

The D antigen is usually expressed in 85% of Caucasian subjects; such persons are said to be Rh positive; 25% are therefore Rh negative, that is to say their red cells do not contain D antigen. There are certain variants in the expression of D antigens, which can be linked either with low antigen density, in which case, reference will be made to weak D antigen, or to different or partial antigenicity, in which case reference will be made to partial D antigens. The weak D condition is characterized by the fact that, while the antigen is normal, the number of its sites per red cell is more or less substantially reduced; this condition is transmissible according to Mendel's laws. Partial D phenotypes have been discovered in Rh D positive subjects having seric anti-D antibodies; these partial D antigens can thus be characterized as possessing only a part of the mosaic. Studies carried out with polyclonal and monoclonal antibodies have made it possible to define 7 categories of partial D antigens, a description being provided of at least 8 epitopes constituting the D antigen (LOMAS et al., 1989; TIPETT, 1988).

The importance of anti-Rh D antibodies became apparent with the discovery of the mechanisms leading to the haemolytic disease of the newborn (HDN). This disease corresponds to the different pathological states observed in certain foetuses or in certain newborn children in the event of foeto-maternal blood group incompatibility which is responsible for the formation of anti-Rh D maternal antibodies capable of passing through the placental barrier.

The transmission of Rh positive foetal red cells to a Rh negative mother can, indeed, lead to the formation of anti-D antibodies.

After immunization of the Rh negative mother, the IgG class anti-D antibodies are capable of passing through the placental barrier and fixing on the Rh positive red cells of the foetus. This fixing leads to the activation of the immunocompetent cells via their surface Fc receptors, thus inducing haemolysis of the sensitized foetal red cells. Depending on the intensity of the reaction, several degrees of HDN severity can be observed.

An HDN diagnosis can be made before and after birth. A pre-natal diagnosis is based on the progression of the anti-D antibody level in the mother using a number of immunohaematological techniques. A postpartum diagnosis can be made on the basis of an umbilical cord blood sample by analysing the following parameters: determination of the blood groups of the foetus and of the father; search for anti-D antibodies; haemoglobin and bilirubin quantity determination.

HDN prophylaxis is presently carried out systematically for all women with a Rh negative blood group and who have given birth to a Rh positive child, using injections of human polyclonal anti-D immunoglobulins. The first immunoprophylaxis tests began in 1964. In order for prevention to be effective, the immunoglobulins have to be injected prior to immunization, that is to say within 72 hours following delivery, and the antibody doses have to be sufficient (100 $\mu$g of antibodies administered intraveinously). At present, polyclonal anti-Rh D immunoglobulins are used; these are prepared from the plasmas of volunteers who have been immunized. These immunizations are necessary because they constitute the only sources of anti-Rh D antibodies hitherto available. Male volunteers whose blood group is O Rh negative are regularly immunized with intraveinous injections of O Rh positive red cells. The plasma of these donors is harvested by plasmapheresis, several donations are pooled and they are used in preparing the intraveinously administered anti-D immunoglobulins. The preparation of such immunoglobulins poses problems of two particular kinds:

the immunization of volunteers is limited and subject to controls; no new immunizations can now be carried out owing to the ethical problems posed by such acts;

in France, as in the rest of Europe, the number of immunized donors is too small to ensure a sufficient supply of anti-D antibodies. Furthermore, as a result of this shortage of anti-D immunoglobulins, HDN prophylaxis cannot be carried out under satisfactory conditions, particularly in the course of pregnancies, with the result that hyperimmune plasma is imported from the United States, for example.

To prevent HDN, it has been demonstrated that anti-D antibodies have to be of class IgG, and not IgM, in order for inhibition of the mother's immunization to be efficient. Polyclonal antibodies have long been in use, and SHAW et al (1988) have shown these preparations to contain both IgG1 and IgG3 antibodies. Several reports have shown that anti-D IgG3 antibodies are more efficient than IgG1 antibodies in inducing in vitro phagocytosis by the monocytes and macrophages of red blood cells sensitized with anti-D's (URBANIAK and GREISS, 1980; WIENER et al., 1987; ZUPANSKA et al., 1987; ROZNSGAY et al., 1989; BROJER et al., 1989; HADLEY and KUMPEL, 1989). On the other hand, it has been proven that anti-D IgG1 antibodies induce better results in vitro in Antibody Dependent Cell Cytotoxicity (ADCC) (KUMPEL et al., 1989 b). Several reports have revealed a relationship between the subclass of the maternal anti-D's and the severity of HDN, i.e. their ability to induce lysis of Rh D positive red cells (EKLUND et al., 1988). The severity of the disease tends to correlate with the presence of IgG1 antibodies (PARIMAUD et al., 1985, ZUPANSKA et al., 1989; POLLOCK and BOWMAN, 1890).

A number of studies have resulted in the production of human anti-D monoclonal antibodies for the purpose of replacing the polyclonal antibodies obtained from fractionating plasmas from immunized volunteer donors. These IgG and IgM class antibodies are used in diagnosis for determining the blood groups, but none of them has been used up to now for therapeutic purposes.

Monoclonal antibodies have several advantages: they can be obtained in large quantities at reasonable prices, each lot of antibodies is homogeneous and the quality of the different batches is reproducible as they are produced by the same cell line, which is kept preserved in liquid nitrogen. The safety of the product as regards absence of viral contamination can be guaranteed.

Several publications describe ways of obtaining cell lines producing IgG class human monoclonal anti-Rh D antibodies: BOYLSTON et al., 1980; KOSKIMIES, 1980; CRAWFORD et al., 1983; BRON et al., 1984; DOYLE et al., 1985; MELAMED et al., 1985; THOMPSON et al., 1986; FOUNG et al., 1987; GOOSSENS et al., 1987; KUMPEL et al., 1989 a). The method used generally involves transformation of the B lymphocytes with the Epstein-Barr virus, with or without subsequent fusion with myeloma cells. Patents relating to such monoclonal antibodies and their secretory cell lines have been applied for or granted: RODER, 1981; CRAWFORD, 1982; KAPLAN et al., 1984; ONO et al., 1983; HUGHES-JONES et al., 1986 (a, b); DE BURGH BRADLEY et al. (a, b, c); SAITO et al., 1988. In addition, it has been reported recently that an IgG3 class monoclonal anti-D antibody was efficient in vivo in destroying Rh D positive red cells (THOMPSON et al., 1990).

The prevention of HDN using a mixture of high affinity monoclonal antibodies, of constant nature and quality, would guarantee prophylactic efficiency and would represent substantial progress by comparison with presently used methods.

That is why the present invention aims to provide monoclonal antibodies against the Rh D antigen, hereinafter referred to as anti-D's, and, more precisely, a mixture of two antibodies of different subclasses, intended to ensure reliable prevention of HDN. These antibodies have no cross reactions with the other antigens of the Rhesus system: C, c, E and e.

One of the anti-D antibodies belongs to sub-class IgG1, has a light chain of the Kappa type and a Glm (3) allotype (GRUBB et al., 1970) and recognizes partial D antigens DIII, DV and DVII but not DIV and DVI.

The other anti-D antibody belongs to sub-class IgG3, has a light chain of the Kappa type and recognizes partial D antigens IIIa, IIIc, IVa, Va and Vc, but not category DVI.

These two antibodies have considerable advantages over polyclonal anti-D antibodies extracted from human plasma:

the selected cells produce large quantities of antibodies of constant quality;

the antibodies have a high affinity for the D antigen;

the specificity of the antibodies has been verified in respect of over 1 500 blood samples;

the antibodies recognize all the partial D categories with the exception of DVI.

The invention also relates to the cells producing the antibodies described above, as well as to the process permitting their selection. The anti-D antibodies are produced by heterohybrid cells obtained directly by fusion either with murine myeloma cells or with the cells of a pre-stabilized heteromyeloma, and not by immortalization with the Epstein-Barr virus, as is the case for the great majority of human IgG class anti-D's described in the prior art. This selection technique is particularly advantageous in terms of safety as it makes it possible to produce preparations of antibodies without the potential risks associated with the possible release of the Epstein-Barr virus.

According to a preferred form of embodiment of the invention, selection of the antibody-producing cells is carried out as follows:

B lymphocytes of the peripheral blood of healthy, o Rh D negative donors, immunized with D+ red cells, are fused either with a murine myeloma cell line, or with cells of a human/mouse heteromyeloma line, using the polyethylene glycol method (Gefter et al., 1977);

the hybridomas obtained are selected with a culture medium containing HAT and screened for the production of specific antibodies with the help of D red cells treated with papain, this screening being carried out by microagglutination;

among the positive clones, only those producing IgG's are selected (the IgM's being less efficient in HDN prophylaxis) and are cultivated in a medium enriched with 10% of foetal calf serum;

the clones appear to be unstable, both as regards their multiplication and as regards their antibody production rates, and they have to be re-cloned several times in succession, using the limiting dilution method (Lefkovits et al., 1979) and monitoring IgG secretion using an ELISA test;

the selected clones are then adapted to growth in a serum-free culture medium (to avoid the presence of bovine serum in the final preparation of antibodies) and re-cloned, in this medium, until stable lines with good growth are established;

detailed characterization of the antibody produced by each of these cell lines is then carried out in order to define the sub-type, the specificity and the affinity thereof, so as to select the most suitable cell lines according to the subsequent intended therapeutic use of the antibodies;

the selected cell lines are multiplied in cell culture recipients, and the monoclonal antibodies produced are purified by ion exchange chromatography.

Two particularly interesting cell lines were chosen and a representative sample was filed with the "Deutsche Sammlung von Mikroorganismen und Zellkulturen", the first of these (190/31), producing an IgGI type antibody, under the number DSM ACC 2039, and the second (P3×229 14G4), producing an IgG3 type antibody, under the number DSM ACC 2040, the deposits being made on 5 and 7 May 1992 respectively at the DSM-Deutsche Sammlung von Mikroorganismen und Zellkulturen GmbH, Mascheroder Weg 1 B, D-3300 Braunschweig, Germany.

The invention also relates to a pharmaceutical composition containing a mixture of at least two monoclonal anti-D antibodies, of sub-classes IgG1 and IgG3; this mixture preferably includes from 30 to 70% of IgG3.

More precisely, the pharmaceutical composition according to the invention contains a mixture of the human monoclonal antibody of sub-class IgG1 produced by the heterohybridoma cell line ACC 2039 and of the human monoclonal antibody of sub-class IgG3 produced by the heterohybridoma cell line ACC 2040.

The pharmaceutical composition according to the invention is of a quality superior to that of certain preparations of polyclonal origin which correspond to a mixture of G immunoglobulins of different specificities and which can only be administered, in most cases, intramuscularly. By contrast, the composition according to the invention is a mixture of two monospecific IgG antibodies that can be administered intraveinously.

In addition, in tests conducted in vitro and in vivo, the efficiency of the monoclonal anti-D antibodies is found to be equal, and even superior, to that observed for the polyclonal preparations. Furthermore, different types of treatment have been carried out on the two purified products to ensure that they are completely virus-free. Numerous tests have been conducted in vitro to check the absence of virus or infectious particles in the purified products.

The invention also relates to the use of the monoclonal antibodies as described above in the preparation of diagnostic kits in any acceptable form for the detection of Rhesus D antibodies.

The following examples illustrate the invention without, however, limiting its scope.

Example 1. Selection of anti-D antibody producing cell lines a) Source of the lymphocytes Donors of anti-D (by plasmapheresis) were selected from among subjects in the Rh D negative blood group immunized with O Rh D positive red cells; they regularly received boosts of Rh D positive red cells. After an immunization, 14 days prior to sampling, 450 ml sample of peripheral blood was taken and the mononuclear cells were separated by centrifuging with a density gradient and then washed.

b) Myeloma cells

Two types of fusion were carried out according to the nature of the myeloma cells used.

Murine myeloma cells (P3×63 Ag8 653) having the following characteristics:—deficient in hypoxanthine guanine phosphoribosyl transferase (HGPRT—), —non-Ig-secreting, doubling time in the order of 24 hours.

These murine myeloma cells are currently used to produce murine monoclonal antibodies.

Heteromyeloma $HM_{22}$ cells obtained by prior fusion between human B lymphocytes from non-immunized subjects and cells of murine myeloma $SP_2O$, which is also a myeloma used for the production of murine monoclonal antibodies. These $HM_{22}$ cells possess the same characteristics as the cells of the P3×63 Ag8 653 myeloma.

c) Fusions:

In both cases, the fusions were carried out according to the same protocol. Approximately $10^8$ mononuclear cells taken from an immunized donor were mixed with $3×10^7$ cells of murine myeloma or heteromyeloma. To the cell pellets obtained after centrifuging the cells, polyethylene glycol (PEG) was added to induce cell fusion (GEFTER et al., 1977). The cell suspension was then washed several times and deposited in 96-well culture plates in a selective medium containing 20% of foetal calf serum, (medium hypoxanthine-aminopterin-thymidine or HAT). A suspension of murine peritoneal cells was first placed in the culture wells to promote the development of the hybrid cells. The culture plates were placed in incubators at 37° C. with 5% of $CO_2$.

d) Identification of the antibody-producind cells

The culture supernatants of the 96-well plates were sampled after approximately 3 weeks' culture to reveal the presence of anti-D antibodies. A microagglutination test was carried out in 96-well plates with 100 μl of supernatant and 100 μl of Rh D positive red cells treated with papain. All the heterohybrids showing an antibody activity were re-seeded and cloned.

Thus, from several experiments of fusions with heteromyeloma cells, 43 IgG-producing and 21 IgM-producing hybridomas were recovered. After 12 months' continuous culture, 8 cell lines produced high levels of anti-D. One of the lines produced the $IgG_3$ sub-class and the others, the $IgG_1$ sub-class;

from several experiments of fusions with murine myeloma cells, 25 producing hybridomas were recovered, among which 6 cell lines were stable after several weeks. Three cell lines produced $IgG_1$'s and three produced $IgG_3$'s.

e) Cell cloning

Cloning was carried out using the limiting dilution method which consists in diluting the cells and in placing them in low concentrations in 96-well plates, preconditioned with murine peritoneal cells or with murine thymocytes, in proportions of $10^4$ or $10^5$ cells per well.

Screening the culture media of each well to detect the presence of antibodies was carried out after 2 weeks. The cells of the positive wells were transferred to larger culture plates and the stability of their growth rates and their antibody production were monitored over a period of time.

Several successive cloning steps were required in order to obtain stable cell lines.

The selected hybridomas were then adapted to growth in a serum-free medium to ensure that the antibody finally harvested was free of any foreign proteins (such as albumin or bovine IgG's). The adaptation process was carried out stepwise, the serum concentration being gradually reduced and transferring being added to the medium as the only protein additive.

f) Creation of cell banks

After obtaining a cell line the production of which was stabilized by cloning, and by larger scale multiplication, in the absence of a feeder cell layer, the cells were maintained in the exponential phase of growth until they were crypreserved. After the cells had been washed with centrifuging, the cell bottoms were recovered in a medium at +4° C. containing pure foetal calf serum with 10% of DMSO (dimethylsulphoxide).

Approximately $5×10^6$ cells were cryopreserved per freezing ampoule in a volume of 1 ml. The ampoules were first deep-frozen at −80° C. and then stored in liquid nitrogen. The cell banks were then validated by conducting several controls: a bacterial, fungal and mycoplasma sterility test; an assessment of cell viability after thawing out; and an assessment of the stability of production by cloning in limiting dilution.

Example 2. Production and purification of the antibodies

After the ampoules of the validated cell banks had been thawed out, the cultures of heterohybrids were innoculated successively in culture flasks, and then in a system equipped for stirring (Spinner), and subsequently in 2, 10, 20, 80 and 250 or 320 litre cell culture recipients. Cell culture recipients are tanks made of glass or stainless steel equipped with a heating system, a system for stirring by rotation and systems for regulating the temperature, the pH and oxygen consumption (measurement of dissolved oxygen partial pressure). The operation of this apparatus meets the requirements of very strict procedures that are scrupulously effected and recorded. Depending on the quantities of antibody to be produced, harvesting is carried out in a single operation, or by drawing off every day a quantity equivalent to approximately 20% of the volume of the cell culture recipient, or by continuous harvesting with retention fermentors. The culture supernatants are then pooled, clarified and concentrated using an automatic ultrafiltration system. After sterilizing filtration through a 0.2 µm filter, the concentrated supernatants are deep-frozen and stored at −35° C.

The monoclonal anti-D antibodies were purified using a complete, fully automated, biocompatible low pressure liquid chromatography apparatus (PHARMACIA). All the columns in the system can be washed in situ and disinfected using procedures currently applicable. The different steps used to purify the anti-D antibodies are as follows:

- disinfection of the automatic apparatus and the purifying gels;
- first chromatography of the antibodies on a cation exchange column (S Sepharose Fast Flow$^{(M)}$, Pharmacia) with elution of the antibodies by a 50 mM phosphate buffer, with a pH 6.8 and NaCl concentrations of 88 mM or 150 mM;
- concentration of the antibodies by tangential filtration, followed by dialysis;
- sterilizing filtration on a 0.2 µm filter;
- viral inactivation by mixing with 13% by volume of a solution of Tween 80 (0.3%)+Tn BP (1%) (Tri-n-butylphosphate) for 6 hours at 24° C. with constant stirring;
- second chromatography step on an S Sepharose Fast Flow$^{(M)}$ gel (Pharmacia) using the same technique as above. The eluates are diluted to ⅓ in a 50 mM phosphate buffer at a pH 7.35;
- third chromatography step on an anion exchange column (S Sepharose Fast Flow$^{(M)}$ gel—Pharmacia). The antibodies are eluted from these gels with a 50 mM phosphate buffer at a pH 7.35 containing 1M NaCl;
- concentration of the antibodies by tangential filtration and then dialysis of the antibodies against 16 volumes of 0.15M glycine buffer at a pH 7.35 with 0.45% of NaCl;
- dilution of the antibodies thus purified in the same glycine buffer;
- sterilizing filtration on 0.2 µm filters.

After these various purification steps, the antibodies were dispensed under sterile conditions in 5 ml borosilicated glass bottles. The bottles were stored in the dark at +4° C.

Example 3. Properties of the monoclonal anti-D antibodies

Using the selection technique described in example 1, and taking account of the prior art, two human monoclonal anti-D antibodies were selected from over 20 anti Rh D antibodies on the basis of their specificity, their intrinsic properties and their functional activity in vitro:

- the antibody produced by the heterohybridoma P3×229 14 G4, of sub-class IgG3, hereinafter referred to as P3×229;
- the antibody produced by the heterohybridoma 190/31, of sub-class IgG1, hereinafter referred to as 190/31.

The 190/31 cell line was selected for its production of 1.5 µg per $10^5$ cells per day. The P3×229 cell line was selected for its production of 2.3 µg per $10^5$ cells per day. (Production is a mean value calculated over a period of 6 weeks, and measurements are carried out using ELISA).

3.1—Specificity of the antibodies

The specificity of the two antibodies selected was first determined using a number of immunohaematological techniques, and on numerous phenotyped blood samples in the different blood group systems.

Analysis of specificity using a small panel

Several agglutination reactions were carried out on a panel of 8 group O blood samples phenotyped and representative of the normal phenotypes.

Reaction involving direct haemagglutination with red cells replaced in suspension in an isotonic saline medium after 1 hour's incubation at 37° C. with the anti-D's and centrifuging;

Reaction involving direct haemagglutination with red cells pretreated with papain (7 minutes at 37° C.) for 35 minutes at 37° C. with the anti-D's and centrifuging;

Indirect Coombs reaction, which consists in pre-incubating red cells in a saline medium at 37° C. for 1 hour with the anti-D's, and then, after washings, adding a human anti-IgG immunoglobulin and reading the agglutination values after centrifuging.

analysis of specificity using a larger panel

The specificity of the antibodies was confirmed on a selected panel of 100 blood samples known and phenotyped using papain treated red cells and the indirect Coombs reaction.

Furthermore, a broader test was conducted by the Blood Group Laboratory of the CRTS on Groupamatic G 360 equipment using the enzymatic technique (bromelin) and taking at least 15 000 blood samples obtained from previously known and identified voluntary blood donors.

Other tests were carried out with a panel of red cells having partial D antigens and using the agglutination technique with papain treated red cells and the indirect Coombs technique.

These results are summarized in Table I. The two antibodies do not have the same reactivity profile. The combination of the two reagents makes it possible to recognize the majority of the partial D's, with the exception of DVI.

TABLE I

Results of agglutination with partial Rh D red cells treated with papain

| Anti-bodies | CATEGORIES | | | | | | | | |
|---|---|---|---|---|---|---|---|---|---|
| | D IIIa | D IIIb | D IVa | D IVb | D Va | D Vb | D Vc | D VI | D VII |
| 190/31 | +++ | NT | − | − | +++ | +++ | − | − | +++ |
| P3 × 229 | +++ | NT | +++ | +++ | − | − | +++ | − | +++ |

NT: not tested
+++: positive reaction
−: negative reaction

Furthermore, an antibody reactivity test was conducted on slices of human tissues of donors taken from the kidneys, skin, brain, thyroid gland, nerves and arteries. No cross reaction was observed with these antibodies, whereas other anti-D antibodies adsorb on certain types of human tissue.

3.2—Characteristics of the monoclonal anti-D antibodies

Class and sub-class of antibodies

The class and sub-class of the heavy chains and the type of light chains of the antibodies were determined using an immunoenzymological technique:

Antibody 190/31: IgG1 Kappa

Antibody P3×229: IgG3 Kappa

Concentration and titer of antibodies

Several techniques were used to determine the concentration of the purified anti-D antibodies. The results obtained vary according to the technique used; only the values corresponding to the same technique can be compared, given that the tests do not cover the same parameters.

TABLE II

Determining Anti-D concentrations using different techniques

| ANTIBODIES | METHODS | | | | |
|---|---|---|---|---|---|
| | OD | ELISA | BCA | Analyzer | Titer |
| 190/31 | 0.153 | 0.174 | 0.119 | 0.055 | 512 |
| P3 × 229 | 0.142 | 0.112 | 0.104 | 0.047 | 512 |
| 190 + 229 | 0.134 | 0.126 | 0.134 | 0.067 | 512 |

- The values are expressed in g/l (except for the OD's and the titers)
- 190 + 229: mixture in equal quantities of the 2 antibodies, 190/31 and P3 × 229.
OD: mesure of optical density at 280 mm
ELISA: immunoenzymatic technique with a human peroxydase labelled anti-Ig
BCA: protein quantity determination with bicinchoninic acid in the presence of $Cu^{++}$ ions
Analyzer: measurement on an auto-analyzer of the haemolysis of red cells not agglutinated by the anti-D's
Titer: inverse of the last dilution still giving agglutinations with papain treated red cells.

Affinity of antibodies

The affinity of the antibodies was measured using two techniques: a radioisotope method using either a radio-labelled human anti-Ig or directly radio-labelled anti-D's (SCATCHARD, 1949) and a flow cytometry method.

TABLE III

Mean values of affinity constants of the monoclonal anti-D antibodies

| ANTIBODY | AFFINITY CONSTANT, L/MOL |
|---|---|
| 190/31 | $1.3 \; 10^{10}$ |
| P3 × 229 | $8.0 \; 10^{9}$ |
| 190 + 229 | $1.8 \; 10^{10}$ |
| Polyclonal | $2.8 \; 10^{9}$ |

3.2—Activities of anti-D antibodies in vitro

To be usable for therapeutic purposes, anti-D antibodies have to be capable of inducing haemolysis, or more precisely, elimination of Rh D positive red cells. The functional properties of such antibodies can be tested in vitro by carrying out several tests: adherence and phagocytosis by macrophages (ZUPANSKA et al., 1987) and antibody dependent cell cytotoxicity (ADCC) tests.

Adherence and phagocytosis tests

The ability of the anti-D antibodies to induce the formation of rosettes on the surface of monocytes and macrophages is evaluated after the incubation of these cells with O Rh D positive red cells pre-sensitized with the anti-D antibodies. The following cell suspensions were used:
  monocytes separated by adherence at 37° C.;
  macrophages separated by adherence at 37° C. and incubated for 24 hours at 37° C.;
  cells of the U 937 line, of myelomonocyte origin.

Antibody dependent cytotoxicity tests

These tests consist in measuring the percentage of specific lysis by human mononuclear cells (effector cells) of Rh D positive red cells pre-labelled with $^{51}Cr$ and pre-sensitized with anti-D antibodies (target cells).

TABLE IV

Relative activities of anti-D antibodies during in vitro tests

| Antibodies | Rosettes * | | | ADCC |
|---|---|---|---|---|
| | Monocytes | Macrophages | U 937 | % lysis |
| 190/31 | 40 | 40 | 40 | 46 |
| P3 × 229 | 68 | 70 | 80 | 51 |
| 190 + 229 | 70 | 75 | 60 | 66 |
| Polyclonal | 50 | 50 | 52 | 64 |

* The results are expressed as a percentage of cells that have fixed at least 2 red cells (anti-D 4 µg/ml). ADCC: antibody dependent cell cytotoxicity (4 µg/ml).

Anti-D activity tests were conducted, varying the proportions of the two antibodies in the mixture, with IgG3 concentrations of 50%, 33% and 10%. During the tests, IgG3 alone always yielded better results than IgG1 tested alone. In addition, the volume to volume mixture of the two antibodies most often yielded higher values in the adherence and ADCC tests. The two sub-classes of antibodies probably recognize different epitopes of the D antigen and their mixture enhances detection sensitivity.

For these various reasons, a volume to volume mixture of the two antibodies was chosen to form the final product, intended for therapeutic use.

BIBLIOGRAPHY

Boylson, J. M., Gardner, B., Anderson, R. L. and Hughes-Jones, N. C. Production of human IgM anti-D in tissue culture by EB virus-transformed lymphocytes. Scand. J. Immunol. 12:355–358 (1980)

Brojer, E., Merry, A. H. and Zupansky, B. Rate of Interaction of IgG1 and IgG3 sensitized Red Cells with Monocytes in the Phagocytosis Assay. Vox. Sang. 56:101–103 (1989)

Bron, D. , Feinberg, M. B., Teng, N. N. H. and Kaplan, H. S. Production of Human Monoclonal IgG Antibodies against Rhesus (D) Antigen. Proc. Nat. Acad. Sci. USA 81:3214–3217 (1984)

Crawford, D. University College London, GB. Human Monoclonal Antibody against Rhesus D Antigen. GB 82:26513 (17.09.82)

Crawford, D. H., Barlow, M. J., Harrison, J. F., Winger, L. and Huehns, E. R. Production of human monoclonal antibody to rhesus D antigen. Lancet, i:386–388 (1983)

De Burgh Bradley, B. A., Doyle, A. and Kumpel, B. M. (a) Central Blood Laboratories Authority, Elstree, GB Human Anti-Rh (D) Monoclonal Antibodies PCT/GB88/00755 WO 89/02442 (18.09.87)

De Burgh Bradley, B. A., Doyle, A. and Kumpel, B. M. (b) Central Blood Laboratories Authority, Elstree, GB Human Anti-Rh (D) Monoclonal Antibodies PCT/GB88/00756 WO 89/02600 (18.09.87)

De Burgh Bradley, B. A., Doyle, A. and Kumpel, B. M. (c) Central Blood Laboratories Authority, Elstree, GB Human Anti-Rh (D) Monoclonal Antibodies PCT/GB88/00757 WO 89/024443 (18.09.87)

Doyle, A., Jones, T. J., Bidwell, J. L. and Bradley, B. A. In vitro development of human monoclonal antibody secreting plasmacytomas. Hum. Immunol. 13:199–209 (1985)

Eklund, J., Jouppila, P. and Seppala, I. J. T. IgG subclasses of Anti-Rh (D) and Hemolytic disease of the Newborn. Vox Sang. 55:51–52 (1988)

Foung, S. K. H., Blunt, J. A., Wu, P. S., Ahearn, P., Winn, L. C. Engelman, E. G. and Grumet, F. C. Human Monoclonal Antibodies to Rho (D). Vox. Sang. 53:44–47 (1987)

Gefter, M. L., Margulies, D. H. and Scharff, M. D. A simple method for polyethylene glycol-promoted hybridization of mouse myeloma cells. Somat. Cell. Genet. 3:231–236 (1977)

Goossens, D., Champomier, F., Rouger, P., and Salmon, C. Human Monoclonal Antibodies against Blood Group Antigens. Preparation of a series of stable EBV immortalized B clones producing high levels of antibody of different isotypes and specificities. J. Immunol. Methods 101:193–200 (1987)

Grubb, R. Molecular Biology, Biochemistry and Biophysics. 9 The genetic markers of human-immunoglobulin. Springer Verlag, Berlin (1970)

Hadley, A, G. and Kumpel, B. M. Phagocytosis by Human Monocytes of Red Cells Sensitized with Monoclonal IgGl and IgG3 Anti-D. Vox Sang 57:150–151 (1989)

Hughes-Jones, N. C., Thompson, K. M. and Melamed, M. D. (a) Central Blood Laboratories Authority, Elstree, GB Production of heterohybridomas for manufacture of human monoclonal antibodies to Rhesus D antigen. GB 86–10106 (25.04.86)

Hughes-Jones, N. C., Thompson, K. M. and Melamed, M. D. (b) Central Blood Laboratories Authority, Elstree, GB Human Anti-Rhesus D Producing Heterohybridomas. EP 0 251 440 (25.04.86)

Issitt, P. D. Genetics of the Rh Blood Group System:Some Current Concepts. Med. Lab. Sci. 45:395–404 (1988)

Kaplan, H. S., Teng, N. H., and Bron, D. G. Board of Trustees of the Leland Stanford Jr. University, Stanford, Calif. 94305 Human Monoclonal Antibody against Rh (D) Antigen and its Uses. PCT/US84/01939 WO 85/02413 (26.11.84)

Koskimes, S. Human Lymphoblastoid Cell Line Producing Specific Antibody against Rh-Antigen D. Scand. Immunol. 11:73–77 (1980) Kumpel, B. M., Poole, G. D. and Bradley, B. A. Human Monoclonal Anti-D Antibodies I. Their Production, Serology, Quantitation and Potential Use as Blood Grouping Reagents. Brit. J. Haemat. 71:125–129 (1989a)

Kumpel, B. M., Wiener, E :, Urbaniak, S, J and Bradley, B. A. Human Monoclonal Anti-D Antibodies. II. The Realtionship between IgG Subclass, Gm Allotype and Fc mediated Function. Brit. J. Haemat. 71:415–420 (1989b)

Lomas, C., Tippett, P., Thompson, K. M., Melamed, M. D. and Hughes-Jones, N. C. Demonstration of seven epitopes on the Rh antigen D using human monoclonal anti-D antibodies and red cells from D categories. Vox Sang. 57:261–264 (1989)

Melamed, M. D., Gordon, J., Ley, S. J., Edgar, D. and Hughes-Jones, N. C. Senescence of a human lymphoblastoid clone producing anti-Rhesus (D). Eur. J. Immunol. 115:742–746 (1985)

Ono, I., Uno, M., Yugi, T. and Uchikawa, M. Mitsubishi Chemical Industries Co., LtD., Japan. Preparation of Monoclonal Antibody to Rh (D) positive Antigen. JP 83-248865 (26.12.83)

Parinaud, J., Blanc, M., Grandjean, H., Fournie, A., Bierme, S. and Pontonnier, G. subclassesIgG subclasses and Gm Allotypes of Anti-D Antibodies during Pregnancy:Correlation with the Gravity of the Fetal Disease. Am. J. Obstet. Gynecol. 151:1111–1115 (1985) Pollock, J. M. and Bowman, J. M. Anti-Rh (D) IgG subclasses and severity of Rh hemolytic disease of the newborn. Vox Sang 59:176–179 (1990)

Roder, J. C. Queens University at Kingston, CDN Human Monoclonal Antibodies. Calif. 82-406033 (29.06.81)

Rozsnyay, Z., Sarmay, G., Walker, M., Maslanka, K., Valasek, Z., Jeffries, R. and Gergely, J. Distinctive Role of IgG1 and IgG3 isotypes in FcyR-mediated functions. Immunology 66:491–498 (1989)

Saito, T. and Kobayashi, M. International Reagents Corp., Japan. Reagents for Determination of Blood Group Substance Rh (D) Factor. JP 88-50710 (03.03.88)

Samdal, H. H., Michaelsen, T. E., Heier, H. E. and Nordhagen, R. Antibody Dependent Cell mediated Cytotoxicity against Anti-D sensitized Human Erythrocytes. APMIS 96:250–256 (1988) Scatchard, G. The attractions of proteins from small molecules and ions. Ann. N.Y. Acad. Sci. 51:660 (1949)

Shaw, D. R., Conley, M. E., Knox, F. J., Khazaeli, M. B. and Lobuglio, A. F. Direct quantitation of IgG subclasses 1,2 and 3 bound to red cells by Rhl (D) antibodies. Transfusion 28:127–131 (1988) Thompson, K. M., Hough, D. W., Maddison, P. J., Melamed, M. D. and Hughes-Jones, N. C. Production of human monoclonal IgG and IgM antibodies with anti-D (rhesus) specificity using heterohybridomas. Immunology 58:157–160 (1986)

Thomson, A., Contreras, M., Gorick, B., Kumpel, B., Chapman, G. E., Lane, R. S., Teesdale,P. Hughes-Jones, N. C. and Mollison, P. L. Clearance of Rh D-positive red cells with monoclonal anti-D. Lancet 336:1147–1150 (1990)

Tippett, P. Sub-divisions of the Rh (D) antigen. Med. Lab. Sci 45:88–93 (1988)

Urbaniak, S. J., and Greiss, M. A. ADCC (K Cell) Lysis of Human Erythrocytes Sensitized with Rhesus Alloantibodies. III. Comparison of IgG Anti-D agglutination and Lytic (ADCC) activity and the Role of IgG Subclass. Brit. J. Haemat. 46:447–452 (1980)

We claim:

1. A human/mouse heterohybridoma cell line having deposit number DSM ACC 2039.

2. A human/mouse heterohybridoma cell line having deposit number DSM ACC 2040.

3. A pharmaceutical composition for the prophylaxis of the haemolytic disease of the newborn which comprises a mixture of human monoclonal anti-RhD antibodies, said mixture including at least a first monoclonal antibody of sub-class IgG1 produced by the heterohybridoma cell line DSM ACC 2039 and a second monoclonal antibody of sub-class IgG3 produced by the heterohybridoma cell line DSM ACC 2040, wherein:

a) each of said cell-lines is not EBV-transformed;

b) each of said first and second monoclonal antibodies recognizes Rhesus D, but not C, c, E and e antigen; and c) said mixture of human monoclonal antibodies permits the detection of partial D antigens, including partial D antigens IIIa and IIIc.

4. A pharmaceutical composition according to claim 3, wherein said mixture of human monoclonal anti-RhD antibodies consists of only said first and second monoclonal antibodies.

5. The pharmaceutical composition according to claim 3, wherein the mixture of antibodies comprises from about 30% to about 70% of IgG3.

* * * * *

UNITED STATES PATENT AND TRADEMARK OFFICE
CERTIFICATE OF CORRECTION

PATENT NO. : 5,851,524
DATED : December 22, 1998
INVENTOR(S) : Beliard et al.

It is certified that error appears in the above-identified patent and that said Letters Patent is hereby corrected as shown below:

On the cover page, change

"[63] Continuation of Ser. No. 196,061, Apr. 5, 1994, abandoned." to

--[63] Continuation of Ser. No. 196,061, Apr. 5, 1994, abandoned, which is a 371 of PCT/EP93/01591, filed June 22, 1993.--

Signed and Sealed this

Thirty-first Day of August, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,851,524
DATED      : December 22, 1998
INVENTOR(S) : Beliard et al.

It is certified that error appears in the above-identified patent and that said Letters Patent is hereby corrected as shown below:

On the title page, item [63], change

"[63] Continuation of Ser. No. 196,061, Apr. 5, 1994, abandoned." to

--[63] Continuation of Ser. No. 196,061, Apr. 5, 1994, abandoned, which is a 371 of PCT/EP93/01591, filed June 22, 1993.--

Signed and Sealed this

Fourteenth Day of September, 1999

Attest:

Q. TODD DICKINSON

*Attesting Officer*        *Acting Commissioner of Patents and Trademarks*